United States Patent [19]

Pellegrino et al.

[11] 4,428,050

[45] Jan. 24, 1984

[54] TANNING AID

[76] Inventors: Frank Pellegrino, 3162 Parsifal Pl., Bronx, N.Y. 10465; Alexander Kalpaxis, 61-17 68 St., Ridgewood, Queens, N.Y. 11385

[21] Appl. No.: 250,181

[22] Filed: Apr. 2, 1981

[51] Int. Cl.³ ............................................. G06F 15/42
[52] U.S. Cl. .................................... 364/414; 364/418; 364/569; 377/20
[58] Field of Search ...................... 364/414, 418, 569; 250/372; 377/20

[56] References Cited

U.S. PATENT DOCUMENTS

| 3,710,115 | 1/1973 | Jubb | 356/226 X |
| 3,987,281 | 10/1976 | Hodes | 364/414 |
| 4,010,372 | 3/1977 | Adler et al. | 250/252.1 X |
| 4,081,664 | 3/1978 | Washizuka et al. | 364/569 X |
| 4,140,391 | 2/1979 | Laciak et al. | 364/569 X |
| 4,218,755 | 8/1980 | Root | 364/715 X |

FOREIGN PATENT DOCUMENTS 1454620  11/1976  United Kingdom ................ 250/372

Primary Examiner—Edward J. Wise
Attorney, Agent, or Firm—Irving M. Kriegsman

[57] ABSTRACT

A portable device is disclosed for monitoring the tanning of an individual in a controlled manner over a series of tanning sessions. The device time integrates the exposure to optical radiation and indicates when predetermined dosages of the radiation have been received for the purpose of obtaining a desired tan. The device which makes use of a personalized program in order to achieve a desired tan includes a series of filters, a light detector, an integrator, a programmable computer and an alarm. Light either from the sun or an artificial light source passed by the filter and impinging on the light detector is converted into electrical signals which are time integrated by the integrator and fed into the computer. In the computer the signals are processed with data signals corresponding to the precalculated radiation dosage limit for each one of a plurality of preselected tanning sessions and the calculated total radiation needed to achieve the desired tan. Each time the radiation dosage for a session is reached the alarm is activated and after the total radiation needed for the tan is reached the alarm is activated. The computer is programmed to activate the alarm at the proper amounts of radiation by entering information personal to the user, such as his skin type, initial tan, desired tan, the type of suntan lotion being used, if any, the number of tanning sessions over which the tan is to be realized and the total exposure time desired for a tanning session. This information is processed to determine dosage amounts. Thus, the device computes a program to follow in order to achieve a desired tan and provides a mechanism for carrying out the program.

7 Claims, 8 Drawing Figures

TANNING AID

BACKGROUND OF THE INVENTION

The present invention relates generally to an electro-optical device for use in conjunction with obtaining a tan and, more particularly, to a programmable electro-optical device for monitoring time integrated exposure to optical radiation and indicating when preselected amounts of such exposure have been realized for the purpose of obtaining a desired tan in a controlled manner over a series of tanning sessions.

Factors which influence the tanning process have been the subject of intense investigation over the past several years due to the fact that excessive exposure to ultraviolet radiation, which is responsible for tanning, can be detrimental to the individual's health. It is now well established that certain regions of the ultraviolet spectrum are capable of inducing skin cancer (i.e. UV-B and UV-C). However, some exposure to solar radiation is beneficial not only psychologically, but also in the production of vitamin D through a photochemical reaction in the skin. Aside from these important medical considerations there are many painful and often embarrassing discomforts which are associated with uncontrolled or unmonitored exposure to solar or artificial radiation.

Obtaining a tan in an unprogramed or unmonitored way can result in erythema, or burning of the epidermal skin layer, giving rise to increased sensitivity and soreness of tender regions of the body such as earlobes, knees, joints, and in general any region of the body which is usually not exposed to solar radiation. The classical sunburn response or erythema begins immediately on exposure, and subsequently disappears. A delayed effect appears after a period of 2–4 hours later, reaching a peak in 14–20 hours subsequent to exposure, and may persist for 24–48 hours. Severe exposure can and indeed often results in desquamation, or peeling of the epidermis which results in a lighter skin pigmentation. Uneven exposure can result in uneven skin coloration. Current interest in "Tanning Salons" has resulted in the extensive use of special lamps which are used in suntan treatment and treatments of psoriasis and other skin disorders through phototherapy. The spectral output of these lamps contains strong emissions in the carcinogenic UV-B and UV-C radiation range. Thus it is extremely important to exercise proper caution when prolonged exposure to radiation for purposes of tanning is desired.

Since the tanning process comprises both an immediate and delayed tanning response, an individual is usually not aware of the delayed or cumulative effects of exposures. It is practically impossible for an individual to visually calibrate or even recognize quantitatively or qualitatively the radiation which is received during a tanning session. Moreover, it is apparent that the quantity of exposure cannot simply be related to the time of exposure, since the latter does not take into account that the intensity of solar radiation is directly affected by such factors as latitude or proximity to equator, altitude above sea level, earth-sun seasonal distance changes, weather conditions, time of day (e.g. UV-B transmission peaks between 10:00 A.M.–2:00 P.M., and is negligible before 8:00 A.M. and after 4:00 P.M.), etc.

Ideally, a knowledgeable sunbather should develop a tanning program or regimen which is based on his individual skin type, and which will include the detection and calibration of his exposure to radiation, ensuring that each tanning session does not exceed the maximum erythemal dose of radiation, which is the dose that his skin type can sustain without injury.

It would also be highly beneficial for the individual to divide his required tanning exposure into the total time available to him for tanning so as to ensure a uniform sequence of exposures over the total tanning period available. In addition, "Tanning Salons" could make use of such a device in order to properly calibrate tans and insure the safe exposure of individuals to the artificial radiation from sun lamps. Thus, it becomes apparent that the achievement of a uniform tan or skin pigmentation in a carefully programmed and calibrated procedure without the hazards of sun burn or other deleterious effects of radiation is a desirable goal.

A number of devices are known for monitoring (human) exposure to UV radiation; however these devices are only for the purpose of preventing excessive exposure or preventing sunburn and not for the purpose of enabling a person to achieve a desired tan in a controlled and programmed manner and based, at least in part, on information personal to the user.

In U.S. Pat. No. 3,710,115 there is disclosed a sunburn warning device comprising radiation detection means, integrator means, measurement means and indicating means to advise the user of the amount of radiation received related to the time of exposure.

In U.S. Pat. No. 3,917,948 there is disclosed a device for measuring the radiation dose of natural and artificial irradiation, in particular in the erythemal-effective range of UV-radiation. The device contains an opto-electronic detector, an analog-to-digital converter and a pulse counter. The device is designed such that different intensities are continuously integrated during a determined period and that the sum of the integrated intensities is evaluated. The device works on one hand as a measuring instrument and on the other hand as an indicator if a predetermined dose is reached, signalling optically or acoustically this event and or shutting off the radiator.

In U.S. Pat. No. 4,016,424 there is disclosed a system for detecting ultraviolet (UV) radiation and particularly adapted for the detection of fire. Electrical pulses are produced at a rate proportional to the intensity of UV energy received by a UV detector tube. An alarm and/or control function is actuated only when the tube pulse rate and pulse rate duration correspond to predetermined values. In addition, the alarm and/or control function is inhibited when the detector tube is exposed to non-fire created UV energy.

In U.S. Pat. No. 4,010,372 there is disclosed a device for measuring the ultraviolet radiation in the UV-A and/or UV-B range with detector means for said ranges, switching means for considering the skin sensitivity, electronic means for evaluating the signals derived from the detector, means for displaying the intensity and/or the dose of the radiation and second switching means for selecting one or different quartz lamps in said ranges. This device is in particular adapted for digitally measuring the dose of harmful erythem effective UV-B radiation or the dose of therapeutic healing UV-A radiation. This invention further relates to a method for producing an calibrating said device, in particular the shunts contained in said second switching means which enables to select different quartz lamps with different line intensities.

In U.S. Pat. No. 4,065,672 there is disclosed an ultraviolet sensing device coupled with suitable electronics which is capable of mesuring the amount of exposure to ultraviolet light.

For purposes of tanning, it is important to realize that the pigmentation of human skin is the result of two factors, intrinsic skin color and inducible skin color. Although intrinsic skin color is genetically determined, induced or facultative skin color is the result of added melanin pigmentation due to solar or artificial exposure to radiation, and the latter's affect on the process of melanogenesis. Melanogenesis referes to the production of melanin by the melanocytes, or pigment producing cells that are found in the epidermis along with the keratinocytes or Malpighian cells which contain the melanosomes.

The term "suntan" refers to the skin color change induced by exposure to solar (or equivalent artificial) radiation. It is now known that UV-B (290–320 nm) is primarily responsible for most of the photobiological responses of the skin, while UV-A (320–400 nm) generally acts to enhance the injury as well as the carcinogenic potential of UV-B radiation. UV-C(200–280 nm), which is by far the most carcinogenic, is not present in the portion of the solar spectrum that reaches the earth due to the presence of ozone in the upper atmosphere which absorbs most of this radiation. Although UV-B is the most efficient radiation for tanning it has also been found to be carcinogenic and may be also highly effective in bringing about premature aging changes in human skin. Kaibey, et al., report that "Long-lasting, esthetically pleasing tans can be induced by irradiation with UV-A alone." Knowledge of the intensity of radiation and the integrated doses of UV-A, UV-B and UV-C is thus not only important for tanning purposes, but also for the prevention of skin cancer or other photobiologically induced skin disorders.

The tanning process may be divided into two distinct photobiological processes, immediate tanning and delayed tanning. Immediate tanning, also known as the Meirowsky phenomemon, involves the oxidation of melanin throughout the epidermis and usually occurs immediately upon exposure to radiation of 320–400 nm (UV-A) and to a lesser extent upon exposure to visible radiation 400–700 nm. Immediate tanning reaches a maximum within 1–2 hours subsequent to exposure and decreases from 3–24 hours thereafter. Immediate tanning basically involves the redistribution of existing melanosomes without production of new melanosomes.

Delayed tanning involves the production of new melanin and disintegration of melanosomes. The effective radiation for the delayed tanning occurs in the UV-B region (which is also responsible for sun burning) of the spectrum (290–320 nm). However it is possible to achieve new melanin formation through the application of larger doses of longer wavelength radiation as high as 700 nm. Pigmentation of the skin due to delayed tanning begins 48–72 hours after exposure to radiation, reaching a peak in 13–21 days, and gradually subsides over the next few months.

Since the structure of melanosomes is genetically determined, the genetic background of the individual determines the extent of melanin production subsequent to exposure to solar or artificial radiation. This genetic background can be divided into five categories.

1. Easy burn and no tan: Blue eyes, very fair skin, red hair, freckled skin.

2. Easy burn and slight tan: blue-green or hazel eyes, moderately fair skin, blond hair.

3. Burn and then tan (without generally burning on subsequent exposures): Brown eyes, brunette or olive skin, medium color skin.

4. No burn and good tan: dark eyes, dark hair (pigmented Caucasians and Orientals).

5. Never burn and markedly tan: markedly pigmented people (Blacks, Australian Aborigines).

The Minimal Erythema Dose (MED), is defined to be that dose of radiation which produces a minimally perceptible erythema or sun burn in an individual. The MED varies with wavelength of radiation. For UV-B radiation the MED for radiation of 290–300 nm is 20–30 $mJ/cm^2$, while the UV-A radiation of 320–400 nm the MED is 20–30 $J/cm^2$.

For the purposes of melanogenesis induction, or tanning, 50–100 $mJ/cm^2$ of UV-B are necessary. Pathak et al., report that an exposure of from 2–5 MED at 297 nm in the UV-B region will produce a grade 2+ pink erythema and a moderate tan, (grade ++, medium brown tan), while an exposure of 10 MED at 297 nm can produce a grade +++, deep brown tan.

It is the general purpose of this invention to provide a device which is programmed to monitor a user's time integrated exposure to artificial or natural radiation and indicate the realization of different amounts of said exposure for the purpose of obtaining a tan in a safe and controlled manner. The device enables the user to follow a calibrated regimen which will result in obtaining a final skin pigmentation (tan) with or without use of filtering agents such as provided in suntanning lotions, or sunscreening devices. The individual initializes the device by entering personal information which will allow the program to classify the individual as to : (1) Individual skin type and sensitivity to radiation; (2) initial skin pigmentation; (3) Sun Protective Factor (SPF) of tanning lotion being used for that session; (4) total exposure time desired for session; (5) final skin pigmentation desired; (6) number of exposures over which desired tan is to be achieved, and any other pertinent factors which affect tanning and which may from time to time be updated in the program.

The device uses the information entered by the individual to determine the following quantities: (1) Total integrated exposure required by individual in order to obtain desired tan; (2) maximum exposure which is allowed for current tanning session (MED); (3) total time of exposure allowed under present conditions of source intensity and SPF lotion used; and (4) SPF factor of lotion that can be used by individual to allow exposure to be extended over desired length of session. The device also includes a "scan" feature which allows an individual to search, with the use of device, that location which will extend or decrease the session time to the desired value. Finally, the device includes an alarm for giving an appropriate warning when the preset dose for each session and the total dosage are achieved, and a preset "turnover" feature which can be used to divide the session into an equal number of intervals for the purposes of tanning the front of the body and the back of the body to the same extent.

SUMMARY OF THE INVENTION

It is an object of this invention to provide a device for monitoring time integrated exposure to UV radiation and indicating the achievement of preselected dosages of such exposure for the purpose of obtaining a desired tan.

It is another object of this invention to provide a device as described above which is portable.

It is still another object of this invention to provide a device as described above which is programmable to respond to parameters personal to the user.

It is yet still another object of this invention to provide a device as described above which provides an indication when the total amount of radiation is received for achieving a desired tan and the maximum amount of radiation that should be received during a particular tanning session and indicating by an alarm when these limits have been realized.

It is a further object of this invention to provide a device that will compute the amount of exposure to UV radiation needed to achieve a desired tan, provide a program of sessions over which the exposure should occur and provide an indication on the completion of such occurrances based on information supplied by the user.

It is another object of this invention to provide a device for enabling a person to achieve a tan in a programmed manner and which minimizes the hazards of UV radiation.

It is still another object of this invention to provide a device which may be used by a person exposed to UV radiation to achieve a tan without subjecting themselves to excessive radiation.

It is yet still another object of this invention to provide a device which can generate a specific program to enable a person to achieve a desired tan and provide indications when specific intervals have been completed.

It is a further object of this invention to provide a device as described above and which can also be used to determine the proper location and/or the proper tanning lotion to use to obtain a desired tan in a safe and programmed manner.

A tanning aid constructed according to the teachings of the invention comprises a UV filter, a light detector, an integrator, a programmable computer and an alarm. The computer includes a microprocessor, a memory and an entry-display. In the use of the device, light passed through the UV filter impinges on the light detector where it is converted into electrical signals whose amplitude is proportional to the intensity of the incoming light. The output of the light detector is time integrated by the integrator. The output of the integrator is fed into the computer which processes the signals and activates the alarm each time the accumulated radiation reaches a preselected level corresponding to the dosage required for a single tanning session and also when the total accumulated radiation reaches the total dosage calculated by the computer to achieve the desired tan.

BRIEF DESCRIPTION OF THE DRAWINGS

In the drawings wherein like reference numerals represent like parts:

FIG. 2 (b) is a front view of a device constructed according to the invention.

DETAILED DESCRIPTION OF PREFERRED EMBODIMENT

Figure 1A:
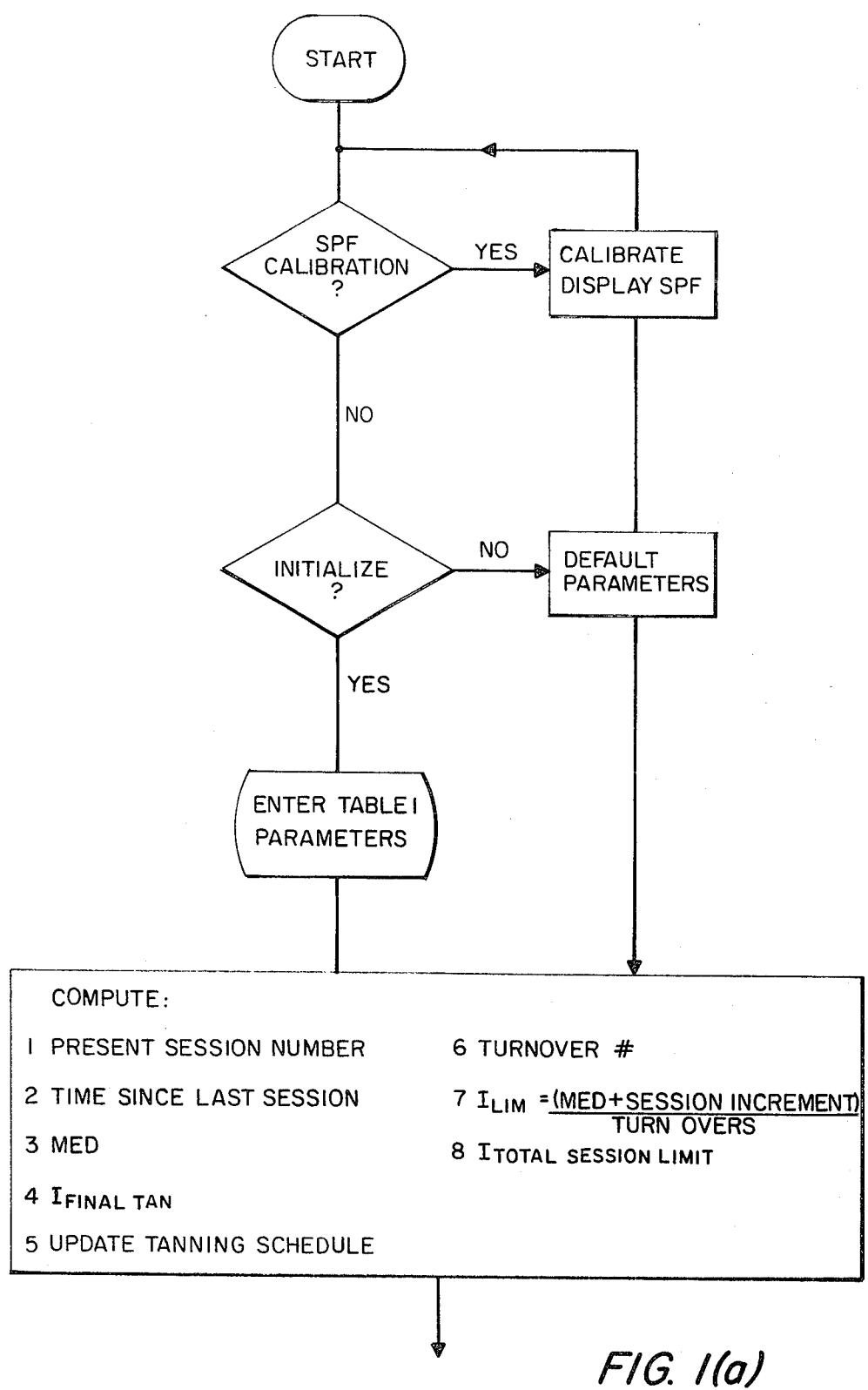
FIG. 1 (includes FIGS. 1(a)–1(d)) is an exemplary flow chart of a scheme for use in obtaining a desired program execution using the device of the invention.
Figure 1B:
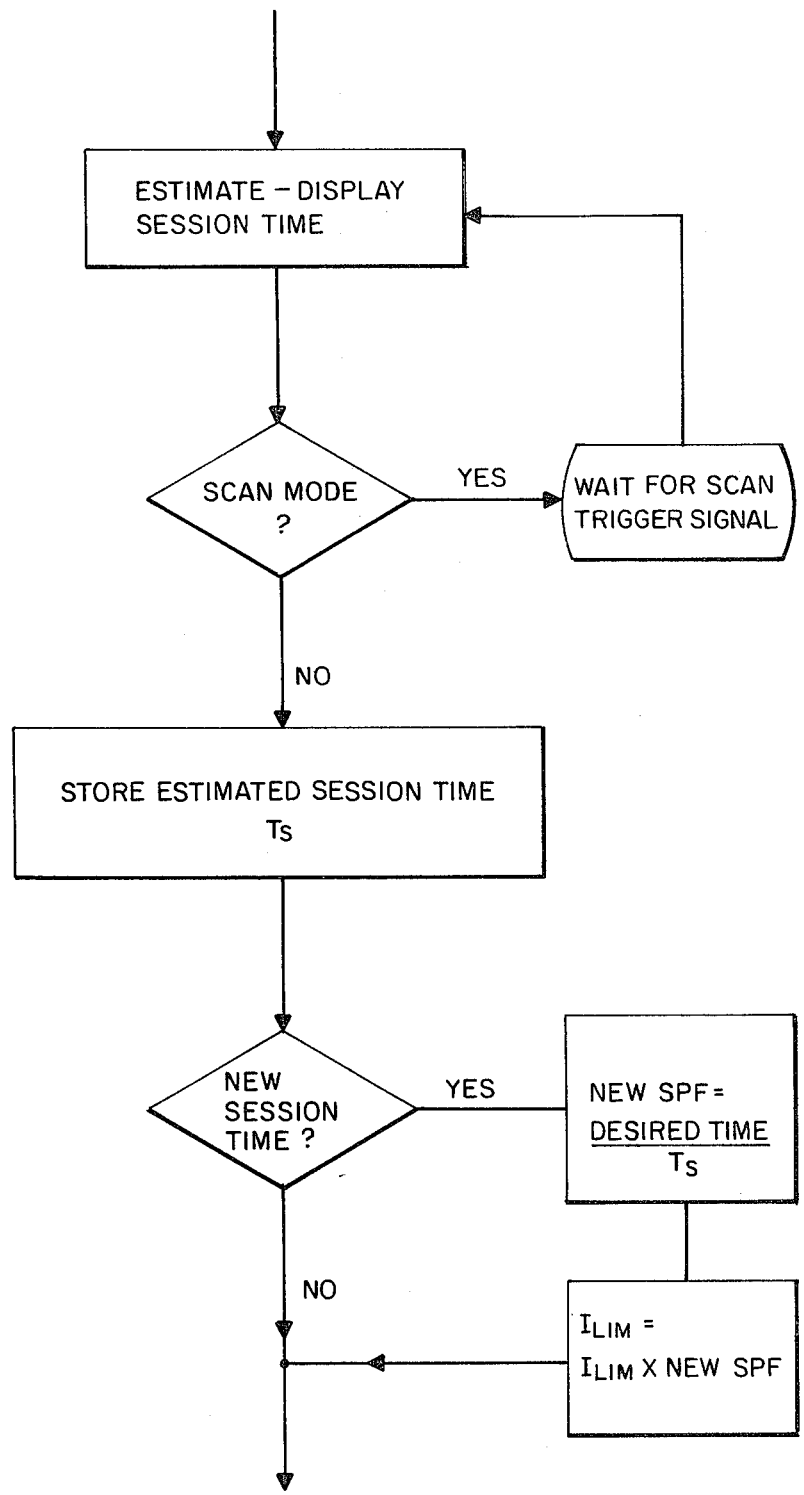
Figure 1C:
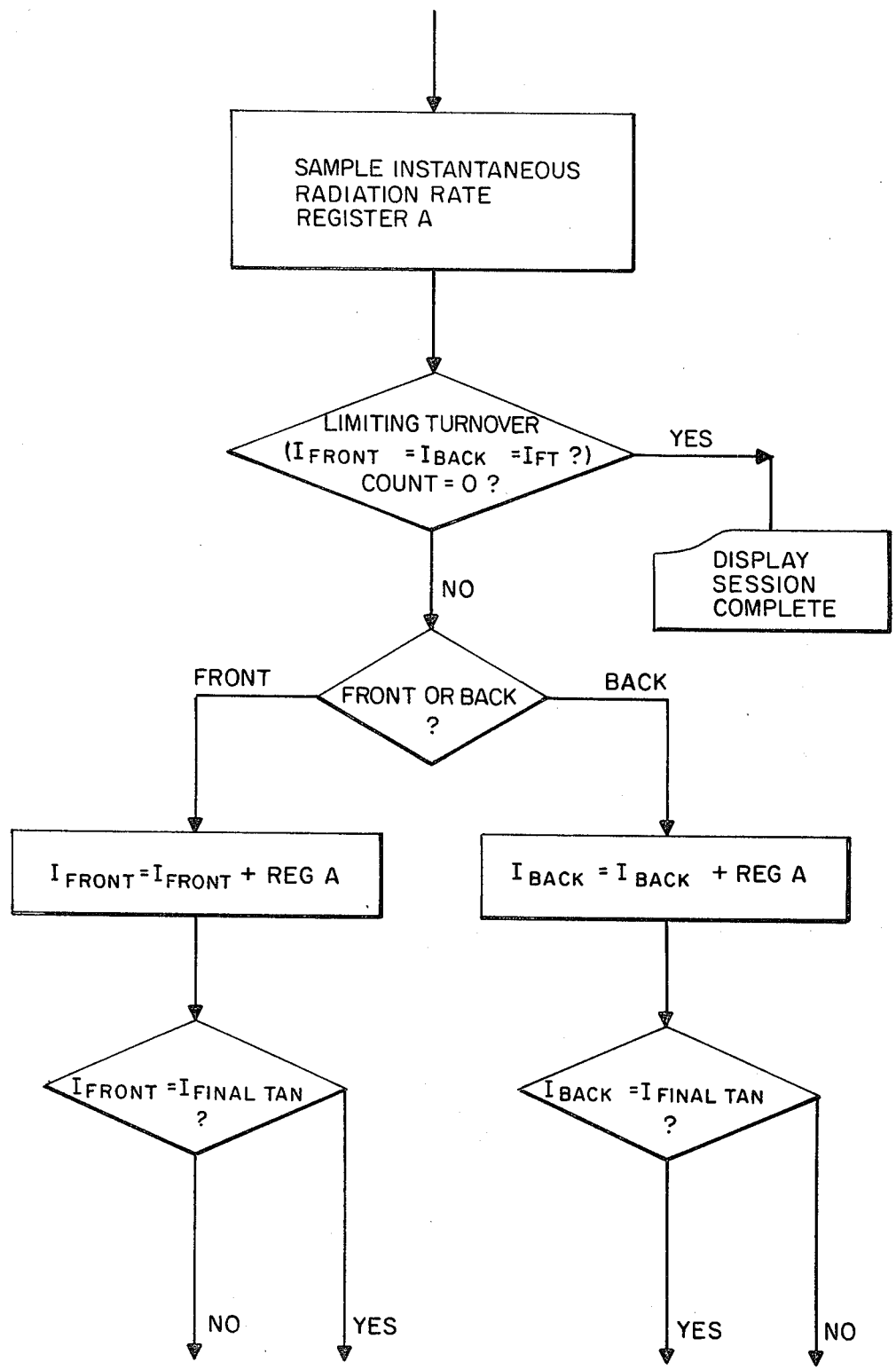
Figure 1D:
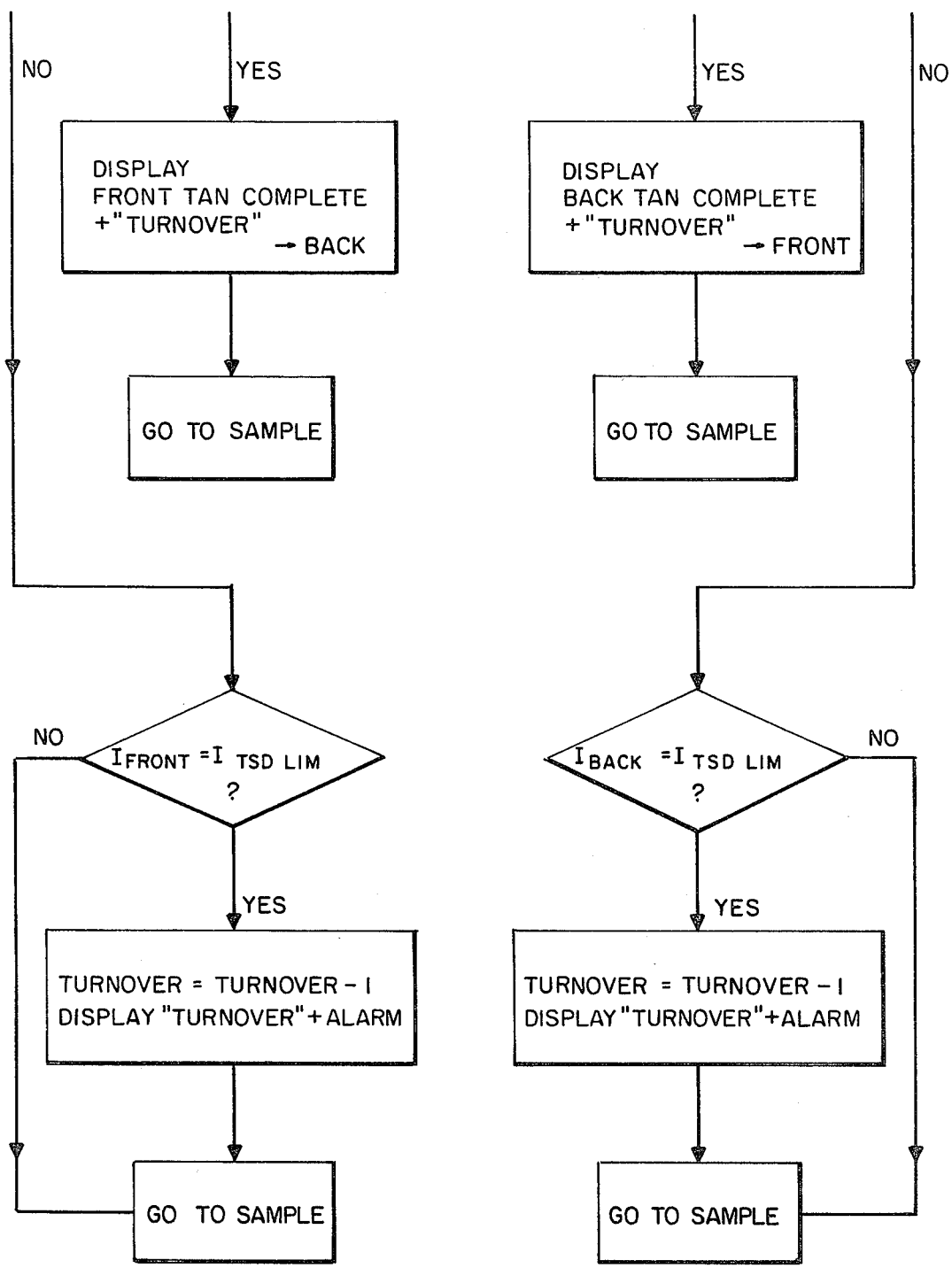

The purpose of the present invention is to provide an individual with a device incorporating a personalized procedure or program which will allow him to obtain a desired tan or skin pigmentation based on exposure to either artificial (i.e. sunlamp) or natural (i.e. solar) radiation in a calibrated manner.

The device includes an optical detector and a programmable computer which executes a program taking as input various factors which influence the tanning process, as well as personal preferences of the individual in the way in which the desired tan is to be achieved and a detector capable of sensing the radiation received by the individual. These factors may include skin type, the SPF of the skin lotion being used, if any, initial skin pigmentation, final skin pigmentation, number of sessions desired and the desired session time.

The operation is initiated by powering the device, which sets the computer into an initialization mode, transferring control to a main program. The program provides for a "menu" driven input of the initialization parameters. The system is initialized by entry of the personal normalization parameters or default values which were either entered in the previous tanning session, or provided as basic default values in the main program. A descriptive flow chart representing one of many possible schemes which can be used to obtain the desired program execution is shown in FIG. 1. Radiation sensed by a detector is time integrated and then fed into a computer where it is periodically compared to two preset limits which are determined by the program. These limits consist of:

1. The maximum daily dose allowed for the individual, or the session radiation dose determined from the tanning program, whichever is less; and 2. the total radiation dose required to achieve the desired tan.

The graduated maximum daily doses allowed are determined by the computer program upon initalization of the individual parameters noted above. This is obtained by adding fractional exposure doses to the MED limits (established in the medical literature).

The integrated exposure required to achieve the desired tan may be determined by calibrating a statistically significant population of each skin type relative to the amount of radiation required to achieve calibrated skin pigmetations, relative to a determinable color chart of possible skin pigmentations.

If the following quantities are defined:

$I_{FT}$ ... the Final Total equivalent integrated exposure intensity required to achieve desired tan, N ... the number of sessions over which total tan is to be achieved, $k_i$ ... the normalization factor of the individual determined from the personal input parameters, $I_{TSL}$ ... the Total Session Limit radiation dose required for the $i^{th}$ session, F (i) ... the tanning weight given to the $i^{th}$ session, and R ... the radiation sampling rate in joules/(cm²-sec).

Then, the session duration time may be estimated from:

$$T_i = \frac{I_{TSL}}{R \times k_i \times F(i)}$$

Upon starting the program, an SPF calibration mode is begun in case the individual wishes to calibrate sun screening materials used as to their screening strengths. The Sun Protective Factor (SPF) is a numerical rating scale which classifies the screening strengths of various tanning lotions available. The SPF factor is multiplicative in that a lotion with a SPF factor of n will allow the individual to receive n times the dose that would be allowed using an SPF factor 1 lotion. Another feature of the device provides for the calibration of sun screening lotions as to actual SPF factor. Under SPF calibration mode, the device calculates SPF factor as:

$$SPF = \frac{I_o \text{ (Intensity w/o lotion)}}{I_L \text{ (Intensity through lotion)}}$$

With reference to the five skin types categorized above, the recommended SPF factors are 8–15 for skin type I, 6–7 for skin type II, 4–5, for skin type III, 2–3 for skin type IV, and 2 for skin type V. Thus, it is possible for a person of skin type V to double his tanning session by merely using a lotion with SPF factor of 4.

The personal parameters noted above are entered or defaulted and the estimated session time is determined. If the estimated session time and location used is not agreeable to the individual, a "scan" mode feature is provided which allows the individual to adjust the intensity input of the radiation by changing one or more of a combination of shading conditions, such as beach umbrella, boardwalk area etc. in addition to the SPF factor of tanning lotion used. In this way, the individual may be able to achieve the desired tanning time by using a combination of factors such as SPF, sun-screens, shading objects, etc. This feature is achieved in the device by dividing the actual radiation integrated per second into the total radiation required for the tanning session. The above procedure is repeated until the desired location, and session period is determined as satisfactory to the individual using the device.

If the estimated session time is not agreeable to the individual and he does not wish to change his location, he may enter the desired time interval of session, and the computer will calculate the new additional SPF required to allow individual to obtain required dose in desired time. This is obtained by entering the desired session time and depressing a special function key which will divide the necessary session time at the current radiation rate into the desired session time.

When the correct combination of location and SPF factors is found, which will allow the obtaining of the required integrated dose for that session during the desired time interval, the program is initiated.

The device is now set down next to the individual (on beach-blanket, or attached by spring clip to bathing suit, etc.). When the required integrated radiation dose for that session is achieved the computer will trigger an audio and/or visual (L.E.D.-Buzzer) alarm to alert user to rotate body 180° to tan (expose) other side of body, repeating as often as required by the tanning program in that session. Thus, since the integrated exposure for either side is monitored within the same limits it is possible to achieve an even tan with the use of the optical tanning computer. In addition, the total radiation dose received for each side is compared to the total session dose (or equivalently the preset number of turnovers is monitored) and the total "Final Tan" dose required. When either of these limits is achieved an appropriate signal is displayed and alarm given.

The above procedure is repeated on subsequent tanning sessions until such time as the "Final Tan" is achieved, with the possibility of renormalizing the tanning program if a different total number of tanning sessions or different final pigmentation color is desired. The renormalization procedure is easily achieved by clearing the continuous memory by depressing a continuous memory clear function key and reinitializing the input parameters noted above.

After each tanning session, upon system shutdown, the computer updates the value of total integrated exposure to date $I_{OT}$, and stores that value in a continuous memory register.

Figure 2A:
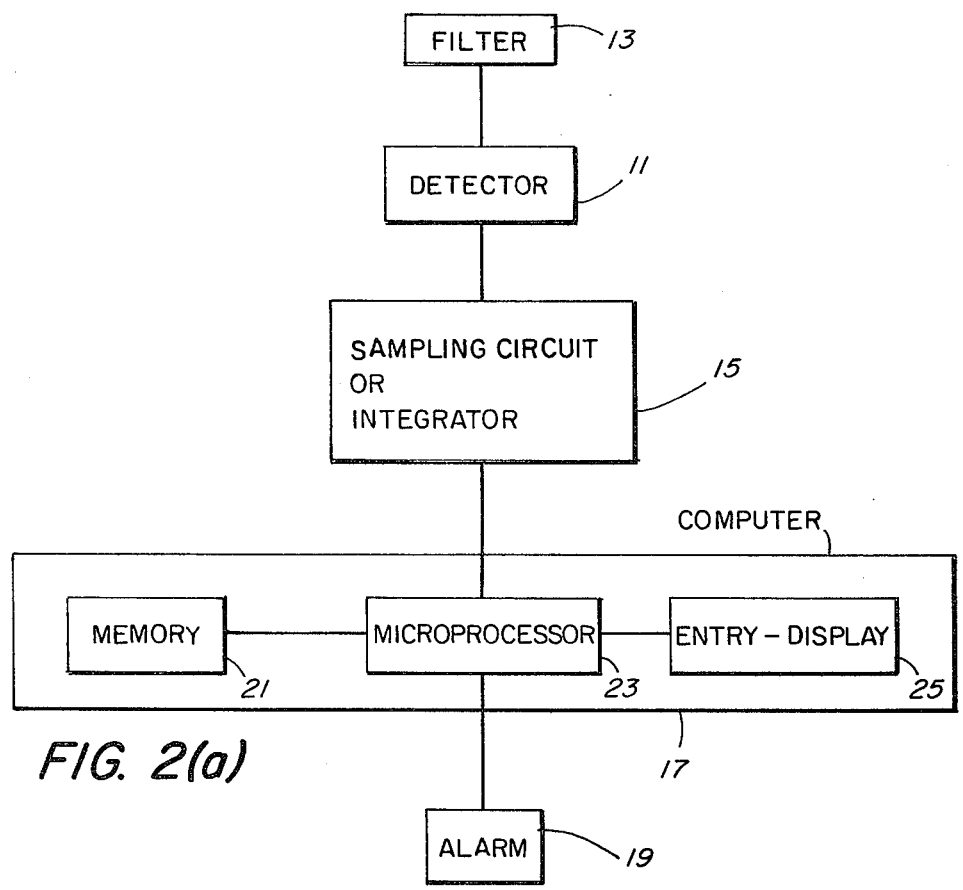
FIG. 2 (a) is a block diagram of a device constructed according to the teachings of the present invention.
Figure 2B:
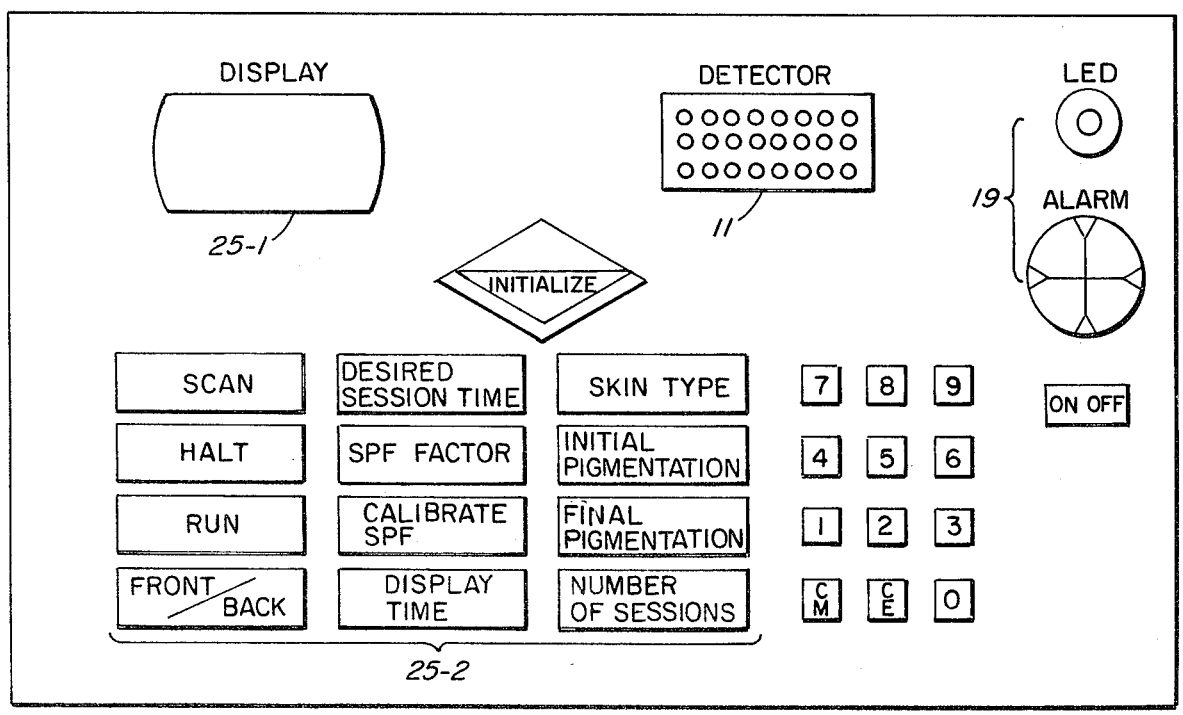

A block diagram of the device and a view of the front of the device are shown in FIGS. 2 (a) and 2 (b) respectively. As can be seen, the device includes a detector 11 which is screened by an appropriate filter 13 to accept only light in the region of interest, such as for example UV-B. Alternatively, instead of a single detector and a single filter, the device may comprise three detectors and three filters, one detector and filter set arranged to measure UV-A radiation, another detector and filter set arranged to measure UV-B radiation and the third detector and filter set arranged to measure UV-C radiation. Also, instead of three detectors and three filters, the device may comprise a single detector and three filters, with each one of the filters being successively moved in front of the detector. The output of detector 11 is coupled to an integrator 15 which time integrates the output from detector 11 to produce a pulse train having a pulse repetition frequency proportional to the instantaneous intensity of the radiation impinging on detector 11. The output of integrator 15 is fed into a computer 17 which is coupled to an alarm 19.

Computer 17 includes a memory 21, a microprocessor 23 and an entry-display unit 25 having a display 25-1 and a key-board 25-2.

Computer 17 can comprise any of the many currently available programmable devices which are portable and which possess an adequate number of registers or memories which are needed to store the parameters used in the tanning program. The currently available microprocessors which can easily perform these functions are the Intel 8080, 8080A, 8085, Zilog Z-80, Z-8000, Motorola 6800, National Semiconductor's COPS 402, etc. A programmable calcutator chip such as is currently available in handheld programmable calculators can also be used (e.g. Texas Instruments TI 59, Hewlett Packard's HP 34C). Such microprocessors when combined with appropriate Random Access Memory (RAM), Read Only Memory (ROM), continuous memory and a keyboard and a display may be used for computer 17.

The description and operation of microprocessors is well documented in the literature and will not be presented here. Moreover the actual computer used is not a determining factor in the operation of the invention herein described, since most of these computers would provide more power and capabilities than are necessary for the operation of the device.

Detector 11 can be any photodetector such as a CdS photocell, photodiode, photomultiplier, etc., that can detect radiation in the region from 250–700 nm. Filter 13 is a narrow band filter capable of selecting radiation in the wavelength region of interest. Filter 13 may be a 0.15 mm plastic film which cuts off radiation below 315 nm. Alternatively, multiple filters and photodiodes can be used to select or isolate different spectral regions such as the UV-A, UV-B and UV-C. These regions can be monitored individually and in ratio form so as to provide warning or registering of relative doses of radiation. Integrator 15 may comprise a simple RC circuit coupled to and controlling the frequency output of an oscillator such as is available in many standard integrated circuits (e.g. National Semiconductor NE-555 timer); thus providing for an intensity reading in digital clock pulses which may be directly summed.

Integration of the clocking pulses of the oscillator is achieved by merely sequentially adding these values in one of a plurality of registers A-N register of the computer 17. Thus a running total integrated intensity reading is available in the computer 17 and may be stored in a register, for example Register A.

Registers B-G in computer 17 may contain the initialization parameters which are required by the program and which are either entered by the user or set to default values. The contents of the registers may be as follows:

Register A: Current exposure rate value
Register B: Skin type of user
Register C: SPF factor of lotion being used
Register D: Present skin pigmentation (or tan) of user ($I_{OT}$)
Register E: Final skin pigmentation desired
Register F: Number of tanning sessions desired
Register G: Desired length of present tanning session
Register H: "Final Tan" dose limit ($I_{FT}$)
Register I: Current Total Session Dose (front or back) ($I_{TSD}$)
Register J: Interval dose limit=Session limit/preset turnovers
Register K: Current Integrated session dose for back
Register L: Current Integrated session dose for front
Register M: Total Integrated dose for back
Register O: Total Integrated dose for front
Register N: Any other parameters which may be found to influence the tanning process and which can be incorporated in the program being run in the device.

Alarm 19 may be a buzzer which provides an audio signal and/or an LED which provides a visual signal.

Figure 3A:
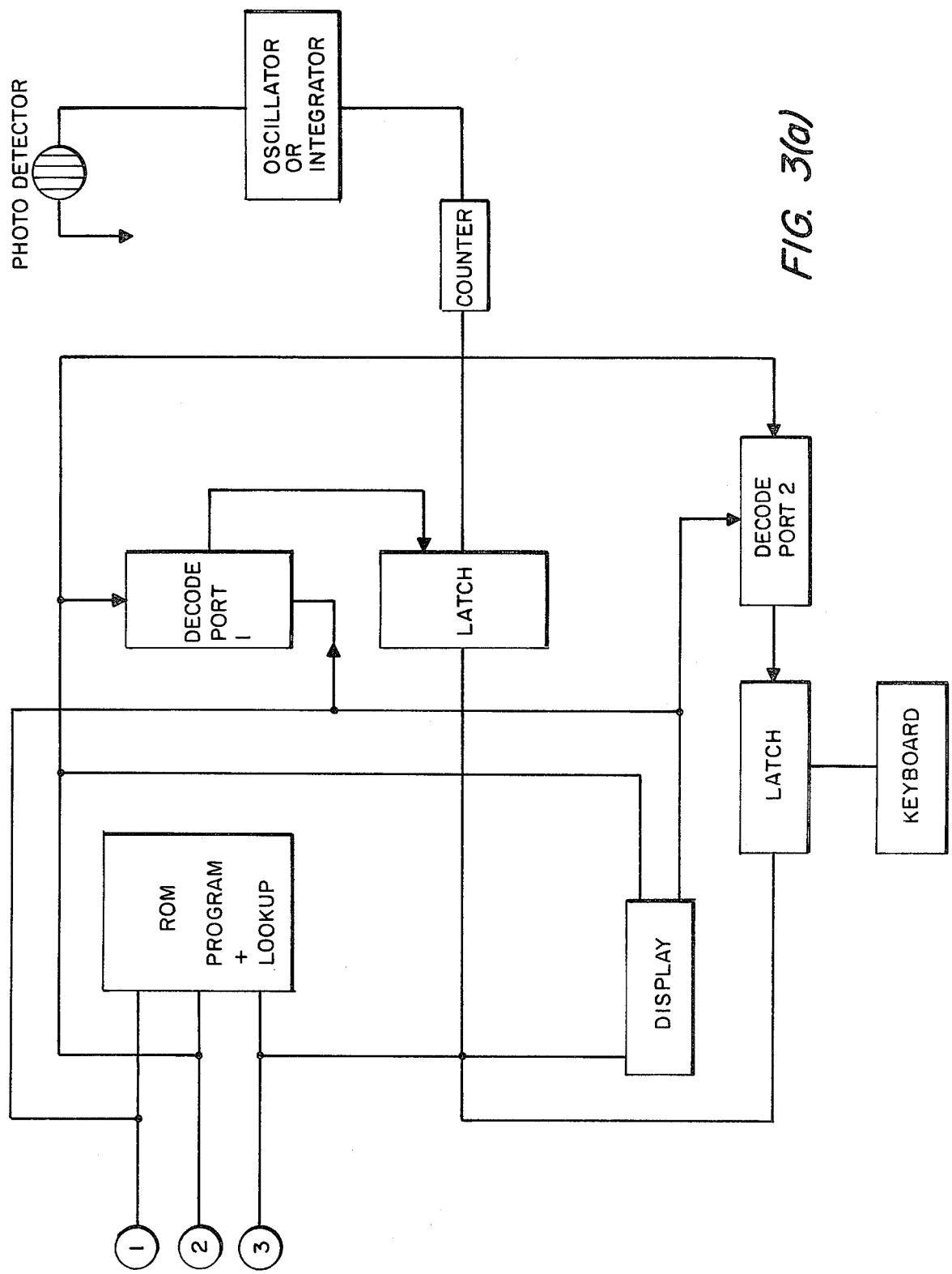
FIG. 3 (includes FIGS. 3(a)–3(b)) is a more detailed block diagram view of the invention.
Figure 3B:
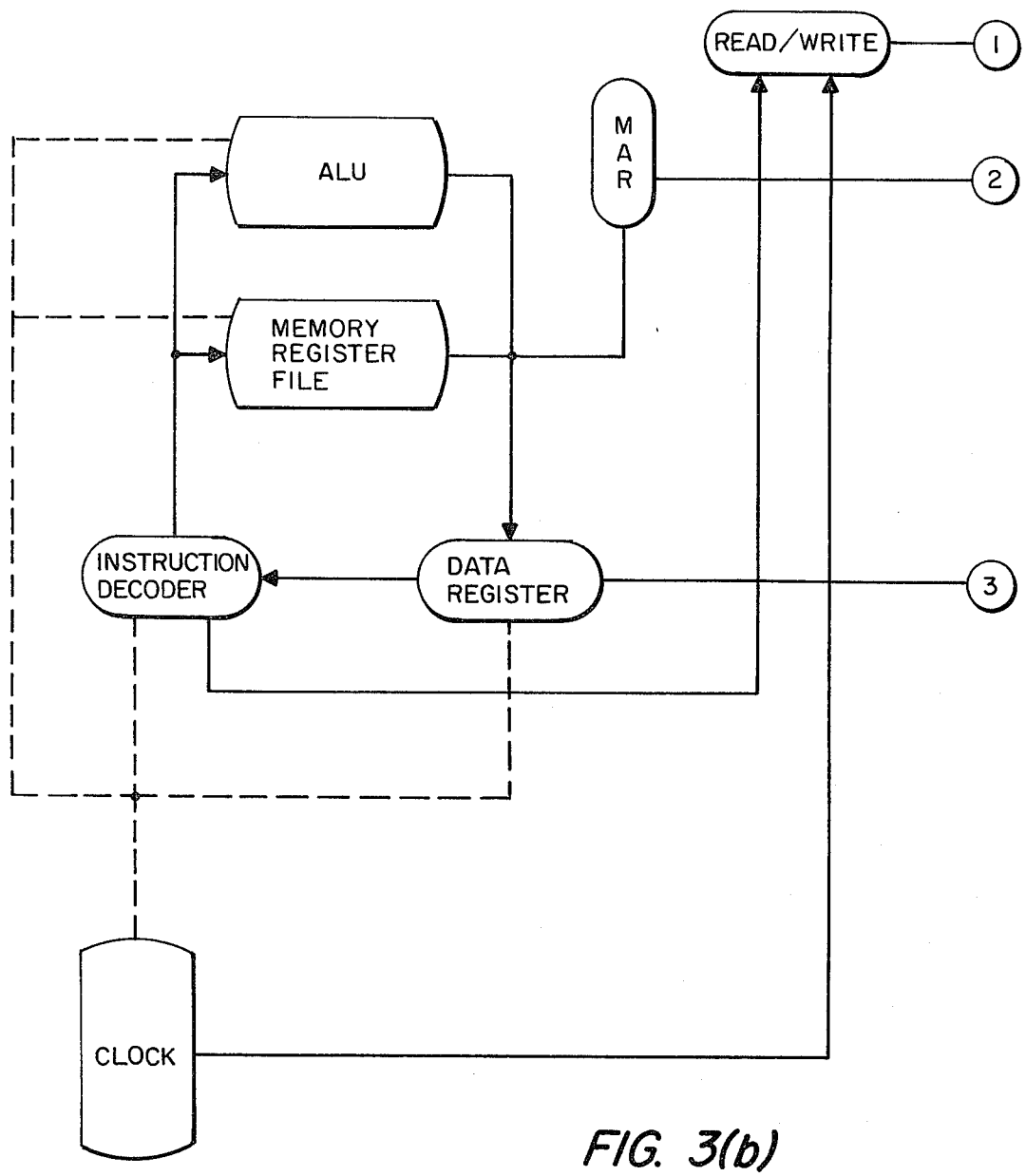

A more detailed diagram of the invention is shown in FIG. 3.

A typical tanning scheme can be described as follows:
Session #1
 ½ MED front, then
 ½ MED back, then
 ½ MED front, and then
 ½ MED back
Session #2
 ½ MED+SPF×5 min front, then
 ½ MED+SPF×5 min back, then
 ½ MED+SPF×5 min front, then
 ½ MED+SPF×5 min back, then
Session #3
 ½ MED+SPF×10 min front, with 4 turnovers
Session #4
 ½ MED+SPF×15 min front, with 4 turnovers
Session #5
 ¼ MED+SPF×15 min. front, with 8 turnovers The program determines the current session interval dose, total session dose, and "Final Tan" dose required by user in order to enable him to obtain the desired tan. This is achieved by referencing the user entries to a look up table, or generates the limit parameters from a determinable formula stored in a ROM. Optionally the program may be written such that the user enters his own limit values directly.

These values are stored in available registers, for example registers H-O. The program constantly (e.g. every sec.) compares the values of register A with those of registers H-O, giving an appropriate display or alarm 19 when equality is achieved between Register A and any of the appropriate registers H-O as determined by the program. The warning is activated by outputting a value to the alarm output line. This will cause alarm 19 and/or the L.C.D.-L.E.D. display to be activated signaling the achieving of the corresponding limit. The user is now either instructed to turn on other side, terminate tanning session, or the entire tanning program (if the "Final Tan" is achieved), and can optionally display total radiation received.

The device may provide special features which can be obtained by special function keys on the keyboard. The main program continuously samples the keyboard keys as in the case of all keyboard reading devices. When a special function key is depressed the program advances to the appropriate subroutine. The subroutines which will perform the SPF factor calibration and the estimated session time based on radiation intensity "search" mode are described in the general flow chart of FIG. 1.

The operation of the microprocessor 23 to perform all the necessary computational overhead and housekeeping operations inherent in the execution of the program may be as follows: The microprocessor accepts commands and data from the keypad and input line and interprets this information via a program stored in ROM. The processor fetches instructions from the ROM and translates the instructions in an Instruction Decoder. The output of the Instruction Decoder sets the state of the machine. A state may be defined by a number of control operations such as: memory read, memory write, input, output, wait state, etc. A memory read or write operation allows the Central Processing Unit (CPU) to interact with the Read-Write Random Access Memory and ROM.

The Memory Address Register (MAR) addresses the memory for data or instruction. In the Instruction Execute Mode results from the MAR are stored in the Data Register for processing. The instruction execute mode sets the future state of the computer.

When the CPU fetches an instruction word from the ROM, it executes the instruction and stores any results in Random Access Memory (RAM). The arithmetic Logic Unit (ALU) performs all register to register, register to memory and memory to memory manipulations, such as additions, subtractions, and logic operations (AND-OR-INVERT). Each encoded instruction is itself a combination of signals that activates a microsequencer which allows for certain sections of the microprocessor to interact with its internal communication "bus" lines. For example, an instruction such as ADD A,B would activate the ALU and Registers A and B.

The main program is stored permanently in a ROM. All data and RUN- time parameters are stored in RAM or continuous memory and in the microprocessor register block. The main program has a subroutine which accessess the keyboard data and moves this data into assigned memory locations directed by the program. Information is displayed by a series of 7 segment L.E.D. or L.C.D. units which are activated by a subroutine in the main program.

What is claimed is:

1. A portable tanning aid for monitoring the tanning of a person in a controlled manner over a series of spaced apart tanning session comprising:
   a. radiation detection means for detecting radiation received in the UV region of the light spectrum,
   b. integrating means for integrating the output of the radiation detector means and generating therefrom a pulse train having a pulse repetition frequency proportional to the instantaneous intensity of the radiation detection means,
   c. a programmable computer for processing the pulse signals from the integrator means, said programmable computer including a counter for counting pulses, a continuous memory for storing the number of pulses received from one tanning session to the next tanning session and a continuous clock for measuring time between sessions and generating output signals when the number of pulse signals reaches a preselected amount and also at preselected intermediate variable length intervals, and
   d. an alarm responsive to the output signals from the computer.

2. The tanning aid of claim 1 and wherein the computer comprises a microprocessor and an entry-display.

3. The tanning aid of claim 2 and wherein the computer is programmable on inputs personal to the user to calibrate features including the SPF factor.

4. The tanning aid of claim 3 and wherein the alarm comprises a buzzer.

5. The tanning aid of claim 3 and wherein the radiation detection means comprises a filter and a light detector.

6. The tanning aid of claim 3 and wherein the integrator means comprises an oscillator.

7. The tanning aid of claim 3 and wherein the radiation detection means comprises a set of light detectors and filters.

* * * * *